United States Patent

Albright et al.

[11] Patent Number: 5,451,397
[45] Date of Patent: Sep. 19, 1995

[54] BILE ACID SEQUESTRANT

[75] Inventors: Robert L. Albright, Churchville; Eric C. Peters, Lansdale, both of Pa.; Larry W. Steffier, Cherry Hill, N.J.

[73] Assignee: Rohm and Haas Company, Philadelphia, Pa.

[21] Appl. No.: 994,026

[22] Filed: Dec. 21, 1992

[51] Int. Cl.6 .......................................... A61K 31/785
[52] U.S. Cl. ................... 424/78.01; 424/484; 424/486; 424/78.12; 424/78.1
[58] Field of Search ................. 424/78.09, 78.0

[56] References Cited

U.S. PATENT DOCUMENTS

| | | |
|---|---|---|
| 2,845,408 | 7/1956 | Melamed . |
| 2,980,657 | 4/1961 | Melamed . |
| 3,186,973 | 6/1965 | Maeder . |
| 3,308,020 | 3/1967 | Wolf et al. . |
| 3,383,281 | 5/1968 | Wolf . |
| 3,627,872 | 12/1971 | Parkinson . |
| 3,692,895 | 9/1972 | Nelson et al. . |
| 3,749,787 | 7/1973 | Hopworth et al. . |
| 3,769,399 | 10/1973 | Hagerman et al. . |
| 3,780,171 | 12/1973 | Irmscher et al. . |
| 3,787,474 | 1/1974 | Daniels et al. . |
| 3,846,541 | 11/1974 | Howard . |
| 3,943,114 | 3/1976 | Hoke . |
| 3,962,420 | 6/1976 | Seidel et al. . |
| 3,974,272 | 8/1976 | Polli et al. . |
| 4,027,009 | 5/1977 | Grier et al. . |
| 4,057,533 | 11/1977 | Hort et al. ................ 526/264 |
| 4,082,701 | 4/1978 | Fries et al. . |
| 4,139,684 | 2/1979 | Coupek et al. . |
| 4,198,395 | 4/1980 | Simone . |
| 4,211,765 | 7/1980 | Johnson et al. . |
| 4,229,267 | 10/1980 | Steinecker . |
| 4,237,218 | 12/1980 | Monthony et al. . |
| 4,265,879 | 5/1981 | Fields et al. . |
| 4,340,585 | 7/1982 | Borzatta . |
| 4,343,730 | 8/1982 | Becker . |
| 4,359,540 | 11/1982 | McEntire . |
| 4,382,853 | 5/1983 | McCoy . |
| 4,387,017 | 6/1983 | McEntire et al. . |
| 4,393,145 | 7/1983 | Zemp . |
| 4,405,015 | 9/1983 | McCoy et al. . |
| 4,495,367 | 1/1985 | Dammann . |
| 4,528,350 | 7/1985 | Goossens et al. . |
| 4,536,294 | 8/1985 | Guillet et al. . |
| 4,649,048 | 3/1987 | Johnson . |
| 4,673,704 | 6/1987 | Flesher et al. . |
| 4,728,696 | 3/1988 | Phung et al. . |
| 4,731,419 | 3/1988 | Fong . |
| 4,759,923 | 7/1988 | Buntin et al. . |
| 4,788,267 | 11/1988 | Chiao et al. . |
| 4,985,410 | 1/1991 | Conti . |
| 5,114,709 | 5/1992 | St. Pierre et al. . |
| 5,178,854 | 1/1993 | Asami et al. . |
| 5,236,701 | 8/1993 | St. Pierre et al. . |

FOREIGN PATENT DOCUMENTS

| | | |
|---|---|---|
| 385627 | 2/1990 | European Pat. Off. . |
| 459632 | 4/1991 | European Pat. Off. . |
| 519119 | 12/1991 | European Pat. Off. . |
| 85505 | 11/1984 | Romania . |

OTHER PUBLICATIONS

Bartoli, Miichel et al., "Synthese et propriete d'echange anionique de quelques resins de type N–(dialkylaminomethyl)–acrylamide", Die Makromolekulare Chemie, vol. 176, pp. 2579–2593 (1975).

JA 33,411, Mitsubishi Chem Ind KK 29,08,78-JA-105132, Plant Virus Controlling Agent Containing N–substituted Acrylamide Polymer Containing Quaternary Nitrogen.

Copolymerization of N,N'–Hexamethylenedimethacrylamide with N,N'–Dimethylaminoethylmethacrylamide and N,N,N'–Trimethylaminoethylmethacrylamide Iodide, O.P. Kolomeitsev and N,N, Kuznetsova, Institute of High Moleular Weight Compounds, U.S.S.R. Academy of Science, No. 8, 1899–1904, 1971, pp. 2136–2142.

Primary Examiner—Thurman K. Page
Assistant Examiner—P. Kulkosky
Attorney, Agent, or Firm—Kevin E. McVeigh; John E. Taylor, III

[57] ABSTRACT

A bile acid sequestrant having a crosslinked polymeric matrix and having branches supported on the polymeric matrix and providing bonding sites for binding bile acid conjugates to the sequestrant, pharmaceutical compositions containing the sequestrant for treatment of elevated plasma cholesterol level are described.

35 Claims, 1 Drawing Sheet

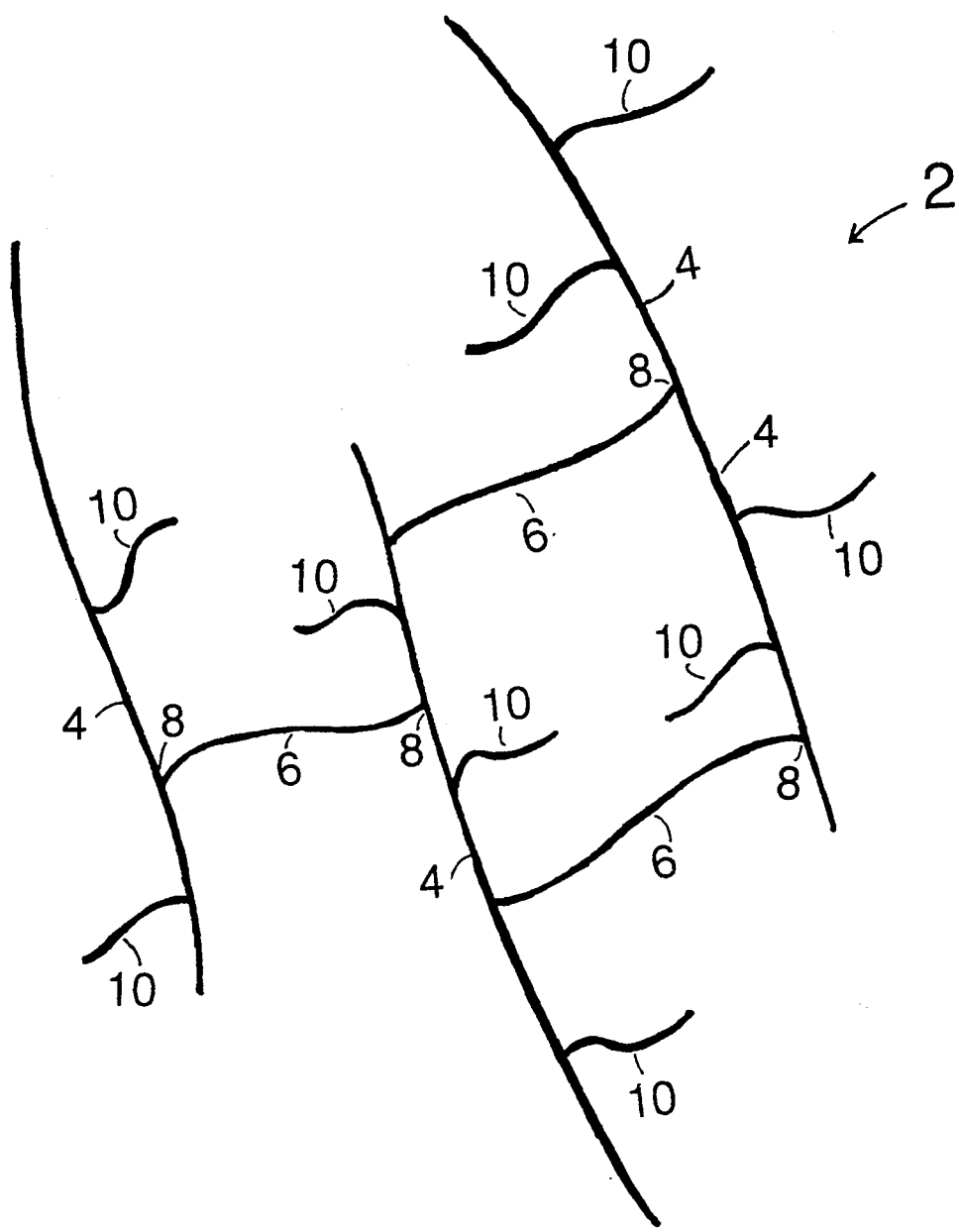

BILE ACID SEQUESTRANT

BACKGROUND OF THE INVENTION

It has been recognized that elevated levels of cholesterol in the blood plasma are a major risk factor of coronary heart disease in humans and that reducing plasma cholesterol level decreases the risk of coronary heart disease.

Cholesterol is a fat soluble steroid that is synthesized in the liver and is also introduced into the body through dietary intake. Cholesterol is present in the blood plasma, in part as the free steroid and in part as a lipid wherein the steroid is esterified with fatty acids, and is a raw material in the biosynthesis of cholesterol derivatives, e.g., bile acids. Bile acids are steroidal compounds, e.g., cholic acid, deoxycholic acid, that are synthesized from cholesterol in the liver and are recirculated, except for a small amount excreted in fecal matter, between the liver and the gastrointestinal tract as conjugates with the amino acids glycine and taurine. The bile acids aid in fat digestion in the intestine.

Plasma cholesterol level reflects a dynamic balance between factors tending to increase plasma cholesterol level, i.e., intake and biosynthesis of cholesterol, and factors tending to decrease plasma cholesterol level, i.e. the conversion of cholesterol to other compounds and excretion of cholesterol derivatives from the body.

Successful approaches to controlling plasma cholesterol level have included dietary modification e.g., minimizing the intake of cholesterol-laden foods and of foods having a high fat content, inhibition of cholesterol biosynthesis and encouraging an increase in the amount of bile acids eliminated from the body.

Particulate resins, e.g., cholestyramine, described in U.S. Pat. No. 3,383,281, and cholestipol, described in U.S. Pat. No. 3,383,281, that are capable of sequestering bile acids are known. Such resins, when orally administered to a mammalian host, form complexes with bile acid conjugates in the intestine and are effective in blocking resorbtion of bile acids from the intestine. The resin and sequestered bile acids are subsequently excreted from the body in fecal matter thereby increasing the rate at which bile acids are eliminated from the body. Other factors being equal, an increase in the rate at which bile acids are eliminated from the body tends to lower plasma cholesterol level by accelerating the conversion of cholesterol to bile acids in order to maintain a constant supply of bile acids. A portion of the cholesterol for this increased synthesis of bile acids is supplied by removal of cholesterol from the blood plasma.

The bile acid sequestrants are orally administered in various forms. Most typically, the sequestrant is taken as a mixture with a food item.

While the capacity of known sequestrants for bile acids is such that dosages effective in lowering serum cholesterol in humans typically fall in the range of about 10 to 15 grams/day, dosages of up to about 50 grams/day may be required. The particulate bile sequestrant resins can be unpleasant to ingest, particularly when large dosages are required. Adverse side reactions such as bloating, gas formation, constipation and diarrhea are common among patients to whom the resins are administered.

There has been a continuing effort in this field to minimize the unpleasant side effects associated with a therapeutically effective bile acid sequestrant regimen by developing sequestrants that have an increased ability to sequester bile acids relative to that of cholestyramine and cholestipol and which are effective in the reduction of serum cholesterol when administered at lower dosages than presently required using cholestyramine and cholestipol.

SUMMARY OF THE INVENTION

A bile acid sequestrant is disclosed. The sequestrant includes a crosslinked polymeric matrix, comprising elongated matrix elements and an effective amount of crosslink matrix elements crosslinked with the elongated matrix elements to render said sequestrant insoluble in water, and branch elements attached to the elongated matrix elements. The elongated matrix elements and attached branch elements being formed by polymeric chains of repeating units. The chains include units having the structural formula:

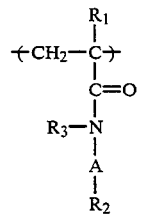

wherein
$R_1$ is H or $(C_1-C_8)$alkyl;
A is

or

$R_2$ is

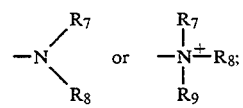

each occurrence of $R_3$, $R_4$, $R_5$, $R_6$, $R_7$, $R_8$, and $R_9$ is independently selected from the group consisting of H and $(C_1-C_8)$alkyl; and a is an integer from 1 to 20;
  b is an integer from 1 to 10;
  d is an integer from 1 to 10; and
  e is an integer from 1 to 5.

The sequestrant includes less than 1.0 weight percent water extractable polymeric chains.

In a preferred embodiment, the sequestrant is the crosslinked polymerization product of a first monomer having the structural formula:

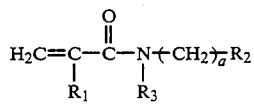

$$-N\begin{matrix}R_7\\ \\R_8\end{matrix} \quad -N^{\pm}\begin{matrix}R_7\\|\\R_8\\|\\R_9\end{matrix};$$

$R_1$, $R_3$, $R_7$, $R_8$ and $R_9$ are each independently H or $(C_1-C_8)$alkyl; and
a is an integer from 1 to 20;
and a second monomer having the structural formula:

$$D\text{-}(E\text{---}\underset{\underset{R_{10}}{|}}{C}\text{=}CH_2)_2$$

or $$F\text{-}(CH\text{=}CH_2)_f$$

wherein
D is $$-(CHR_{11})_g-$$

or $$-(-(CHR_{11})_h O-)_k(CHR_{12})_i-;$$

E is $$-O-$$

or $$-N-\underset{\underset{R_{14}}{|}}{\overset{\overset{O}{\|}}{C}}-;$$

F is phenylene, $(C_1-C_4)$alkylphenylene or benzenetriyl;
each occurrence of $R_{10}$, $R_{11}$, $R_{12}$, and $R_{14}$ is independently selected from the group consisting of H and $(C_1-C_8)$alkyl; and
f is 2 if F is phenylene or $(C_1-C_4)$alkylphenylene, and f is 3 if F is benzenetriyl;
g is an integer from 1 to 20;
h is an integer from 1 to 10;
i is an integer from 1 to 10; and
k is an integer from 1 to 5.

A pharmaceutical composition is disclosed. The composition includes a therapeutically effective amount of the above described sequestrant and a pharmaceutically acceptable carrier.

A method for lowering plasma cholesterol level in a mammal is disclosed. The method includes orally administering a therapeutically effective amount of particles of the sequestrant of the present invention to the mammal.

BRIEF DESCRIPTION OF THE DRAWING

The FIGURE shows a schematic representation of a portion of crosslinked polymer matrix and polymeric branches supported on the matrix.

DETAILED DESCRIPTION OF THE INVENTION

The bile acid sequestrant of the present invention includes a crosslinked polymeric matrix having attached polymeric branches, including branches carrying both a hydrogen bonding site and an ionic bonding site, supported on the matrix.

The FIGURE shows a schematic representation of the microstructure of the polymer matrix and attached branches. The crosslinked polymeric matrix 2 includes elongated matrix elements 4 and crosslink-matrix elements 6. The elongated matrix elements 4 and crosslink-matrix elements 6 are interconnected at nodes 8 to form a 3dimensionally extending polymeric network and to define a complimentary interpenetrating network of interstitial space within the polymeric matrix 2. Branches 10 are supported on the elongated matrix portions.

In a preferred embodiment, the elongated matrix elements 4 and attached branch elements 10 are formed by chains of monomeric units including monomeric units having the structural formula (I):

$$-(CH_2-\underset{\underset{\underset{\underset{\underset{R_2}{|}}{A}}{|}}{\underset{R_3-N}{|}}}{\overset{\overset{R_1}{|}}{C}})- \quad (I)$$
$$\phantom{xxxxxx}C=O$$

$R_1$ is H or $(C_1-C_8)$alkyl;
A is $$-(CHR_4)_a-$$

or $$-(-(CHR_4)_b NR_6-)_e(CHR_5)_d-;$$

$R_2$ is $$-N\begin{matrix}R_7\\ \\R_8\end{matrix} \quad \text{or} \quad -N^{\pm}\begin{matrix}R_7\\|\\R_8\\|\\R_9\end{matrix};$$

each occurrence of $R_3$, $R_4$, $R_5$, $R_6$, $R_7$, $R_8$, and $R_9$ is independently selected from the group consisting of H and $(C_1-C_8)$alkyl; and
a is an integer from 1 to 20;
b is an integer from 1 to 10;
d is an integer from 1 to 10; and
e is an integer from 1 to 5.

As used herein, the terminology "$(C_1-C_8)$alkyl" means a straight-chain or branched-chain alkyl group having one to eight carbon atoms, e.g., methyl, ethyl, n-propyl, isopropyl, isobutyl, t-butyl, neopentyl, t-penty, hexyl, t-hexyl, heptyl, octyl.

In a preferred embodiment,
$R_1$ is H or methyl;
A is $-(CHR_4)_a-$;

$R_2$ is

$R_4$ is H;
$R_7$ and $R_8$ are each methyl; and
a is an integer from 2 to 6.

In a preferred embodiment, the crosslink matrix elements have the structural formula (II) or (III):

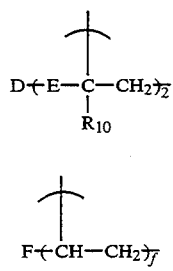

D is

or

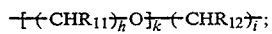

E is

or

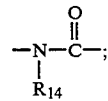

F is phenylene, ($C_1$-$C_4$)alkylphenylene or benzenetriyl; each occurrence of $R_{10}$, $R_{11}$, $R_{12}$, and $R_{14}$ is independently selected from the group consisting of H and ($C_1$-$C_8$)alkyl; and f is 2 if F is phenylene or ($C_1$-$C_4$)alkylphenylene, and
  f is 3 if F is benzenetriyl;
  g is an integer from 1 to 20;
  h is an integer from 1 to 10;
  i is an integer from 1 to 10; and
  k is an integer from 1 to 5.

As used herein, the term "phenylene" means a bivalent aromatic ring of six carbon atoms.

As used herein, the term "($C_1$-$C_4$)alkylphenylene" means a bivalent aromatic ring of six carbon atoms substituted with an alkyl group of one to four carbon atoms and includes, e.g., methylphenylene and ethylphenylene.

As used herein, the term "benzenetriyl" means a trivalent aromatic ring of six carbon atoms.

In a preferred embodiment, the crosslink matrix elements comprise elements having the structural formula (II);
  wherein
  D is $+CHR_{11}\overline{)g}$;

E is

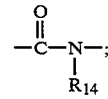

$R_{10}$ is H or methyl;
$R_{10}$ and $R_{14}$ are each H; and
g is an integer from 1 to 12.
In a highly preferred embodiment;
$R_1$ is H or, more preferably, methyl;
A is $+CHR_R\overline{)a}$;
$R_2$ is

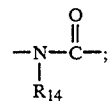

$R_4$ is H;
$R_7$ and $R_8$ are each methyl;
a is an integer from 2 to 6, most preferably, 3;
the crosslink elements have the structural formula (III), wherein:
D is $+CHR_{11}\overline{)g}$;
E is

$R_{10}$ is $CH_3$;
$R_{11}$ and $R_{14}$ are each H; and
g is an integer from 1 to 12, most preferably, 6.

The amount of crosslinking in the sequestrant of the present invention may be any amount that is effective to render the sequestrant insoluble in water while maintaining efficacy as a bile acid sequestrant. Preferably, the amount of crosslinking approaches the minimum amount effective to render the sequestrant insoluble in water while maintaining high efficiency as a bile acid sequestrant.

The sequestrant of the present invention swells with moisture when immersed in an aqueous medium and measurement of the moisture holding capacity of a fully hydrated sample of the sequestrant provides an index of the degree of crosslinking of the sample. As used herein, "moisture holding capacity" means the weight loss exhibited by a fully hydrated sample of sequestrant upon drying at about 105° C., expressed as a percent of the weight of the hydrated sequestrant. A preferred method for measuring the moisture holding capacity of the sequestrant of the present invention is set forth below in Example 27.

The moisture holding capacity of the sequestrant of the present invention is preferably greater than about about 20 percent, more preferably, greater than about about 50 percent and, most preferably, from about 70 percent to about 97 percent, of the weight of hydrated sequestrant.

Noncrosslinked poly(dimethylaminopropylmethacrylamide), while exhibiting high efficacy in lowering plasma cholesterol, has shown evidence of toxicity when orally administered to rats, monkeys and dogs.

The crosslinked bile acid sequestrant of the present invention exhibits reduced toxicity toward mammalian intestinal mucosa relative to linear, i.e., noncrosslinked, poly(dimethylaminopropylmethacrylamide).

In view of the toxicity exhibited by noncrosslinked analogs of the present bile sequestrant, the sequestrant of the present invention must be substantially free of water extractable noncrosslinked polymeric or oligomeric residue. Preferably, the sequestrant includes less than about 1 wt % and more preferably, less than about 0.5 wt % water extractable noncrosslinked polymeric or oligomeric residue.

Preferably, the sequestrant is substantially free of water extractable unreacted monomeric residue. More preferably, the sequestrant includes less than about 50 parts per million (ppm) water extractable unreacted monomer. Most preferably, the amount of residual water extractable unreacted monomer in the sequestrant is less than about 10 ppm.

Preferably, the sequestrant of the present invention exhibits an anion exchange capacity of greater than about 3 milliequivalents/gram dry polymer (meq/g) and, more preferably, greater than about 4 meq/g. In a more highly preferred embodiment, the sequestrant of the present invention exhibits an anion exchange capacity of about 5 meq/g to about 6 meq/g.

When $R_2$ is an amino group, a relatively high proportion, e.g., from about 55% to about 80% of the total number of amino groups, are protonated in situ in the mammalian intestinal tract at a pH of 7.2 and such protonated amino groups support a stable positive charge.

In a preferred embodiment, the sequestrant is in particulate form. Preferably hydrated, i.e., water swollen, particles of sequestrant exhibit a mean particle diameter from about 10 microns to about 400 microns. In a highly preferred embodiment, hydrated particles of the sequestrant exhibit a mean particle diameter from about 10 microns to about 200 microns.

In a preferred method, the bile acid sequestrant of the present invention is made by free radical-initiated precipitation polymerization of a mixture of ethylenically unsaturated monomers from an aqueous phase. Preferably, to reduce swelling of the precipitating polymer, the aqueous phase is a salt solution.

In a preferred embodiment, the sequestrant of the present invention comprises the crosslinked reaction product of the free radical copolymerization of a first monomer having one ethylenically unsaturated site per molecule and a second monomer having two or more ethylenically unsaturated sites per molecule. The elongated matrix elements and attached branches of the sequestrant are formed by chains of repeating units derived from the first monomer and the crosslink elements of the sequestrant are derived from the second monomer.

In a highly preferred embodiment, the first monomer has the structural formula (IV):

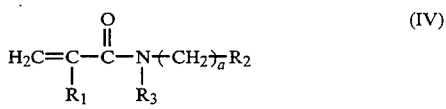

(IV)

wherein $R_1$, $R_2$, $R_3$ and a are defined as above.

Compounds suitable for use as the first monomer of the present invention include amino($C_1$-$C_8$)alkylacrylamides and amino($C_1$-$C_{20}$)alkylmethacrylamides, e.g., aminomethylacrylamide and aminoethylmethacrylamide, ($C_1$-$C_8$)alkylamino($C_1$-$C_{20}$)alkylacrylamides and ($C_1$-$C_8$)alkylamino($C_1$-$C_{20}$)alkylmethacrylamides, e.g., methylaminoethylacrylamide and methylaminoethylmethacrylamide, di($C_1$-$C_8$)alkylamino($C_1$-$C_{20}$)alkylacrylamides and di($C_1$-$C_8$)alkylamino($C_1$-$C_{20}$)alkylmethacrylamides, e.g., diethylaminoethylacrylamide, diethylaminopropylmethacrylamide, dimethylaminoethylacrylamide, dimethylaminoethylmethacrylamide, dimethylaminopropylacrylamide, dimethylaminopropylmethacrylamide, dimethylaminobutylacrylamide, dimethylaminobutylmethacrylamide dimethylaminopentylacrylamide, dimethylaminopentylmethacrylamide, dimethylaminohexylacrylamide and dimethylaminohexylmethacrylamide, and tri($C_1$-$C_8$)alkylammohio($C_1$-$C_{20}$)alkylacrylamides and tri($C_1$-$C_8$)alkylammonio($C_1$-$C_{20}$)alkylmethamides, e.g., trimethylammonioethylacrylamide and trimethylammoniopropylmethacrylamide, as well as mixtures thereof.

Preferably, the first monomer is a dimethylamino($C_2$-$C_6$)alkylacrylamide or a dimethylamino($C_2$-$C_6$)alkylmethacrylamide, i.e., is selected from the group consisting of dimethylaminoethylacrylamide, dimethylaminoethylmethacrylamide, dimethylaminopropylacrylamide, dimethylaminopropylmethacrylamide, dimethylaminobutylacrylamide, dimethylaminobutylmethacrylamide dimethylaminopentylacrylamide, dimethylaminopentylmethacrylamide, dimethylaminohexylacrylamide, dimethylaminohexylmethacrylamide and mixtures thereof.

Compounds suitable as the first monomer of the present invention, e.g., dimethylaminopropylmethacrylamide, trimethylammoniopropylmethacrylamide are commercially available. Compounds suitable as the first monomer that are not commercially available can be made by conventional synthesis methods. Aminoalkylacrylamides and aminoalkylmethacrylamides can be made, e.g., by base catalyzed aminoalkylation of acrylamide or methacrylamide. Alkylaminoalkylacrylamides and alkylaminoalkylmethacrylamides can be made by alkylation of the corresponding aminoalkylacrylamide or aminoalkylmethacrylamide. Dialkylaminoalkylacrylamides and dialkylaminoalkylmethacrylamides can be made, e.g., by treating the dialkylaminoalkylamine with acryloyl chloride or methacryloyl chloride in dimethylformamide using pyridine as an HCl sequestrant. Trialkylammonioalkylacrylamides and trialkylammonioalkylmethacrylamides can be made, e.g., by alkylation of the corresponding dialkylaminoalkylacrylamide or dialkylaminoalkylmethacrylamide by treatment with an alkylhalide. Alternatively, a crosslinked reaction product of the first and second monomer that includes monomeric units derived from a dialkylaminoalkylacrylamide or a dialkylaminoalkylmethacrylamide can be treated with an alkylhalide to form the corresponding trialkylammonio embodiment.

Most preferably, the first monomer is dimethylaminopropylmethacrylamide.

In a preferred embodiment, the second monomer has the structural formula (V) or (VI):

(V)

(VI)

wherein, D, E, F, $R_{10}$, $R_{11}$, $R_{12}$, $R_{14}$, f, g, h, i and k are defined as above.

Monomeric compounds having the structural formula (V) include, e.g., alkyleneglycol divinylethers, e.g., diethyleneglycol divinylether, $(C_1-C_{20})$alkylenebis(acrylamide)s and $(C_1-C_{20})$alkylenebis(methacrylamide)s, e.g., N,N'-methylenebis(methacrylamide), N,N',-ethylenebis(acrylamide) and N,N'-hexamethylenebis(methacrylamide).

Monomeric compounds having the structural formula (VI) include, e.g., divinylbenzene, trivinylbenzene, divinyltoluene and divinylethylbenzene.

Preferably, the second monomer is a $(C_1-C_{12})$alkylenebis(acrylamide) or a $(C_1-C_{12})$alkylenebis(methacrylamide) and, more preferably, is selected from the group consisting of N,N'-propylenebis(acrylamide), N,N'-butylenebis(acrylamide), N,N'-pentamethylenebis(acrylamide), N,N'-hexamethylenebis(acrylamide), N,N'-heptamethylenebis(acrylamide), N,N'-octamethylenebis(acrylamide), N,N'-decamethylenebis(acrylamide), N,N'-dodecamethylenebis(acrylamide), N,N'-propylenebis(methacrylamide), N,N'-butylenebis(methacrylamide), N,N'-pentamethylenebis(methacrylamide), N,N'-hexamethylenebis(methacrylamide), N,N'-heptamethylenebis(methacrylamide), N,N'-octamethylene-bis(methacrylamide), N,N'-decamethylenebis(methacrylamide), N,N'-dodecamethylenebis(methacrylamide), and mixtures thereof.

Most preferably, the second monomer is N,N'-hexamethylenebis(methacrylamide).

Monomers suitable as the second monomer, e.g., N,N'-hexamethylenebis(methacrylamide), are commercially available. Compounds suitable as the second monomer that are not commercially available can be made by conventional synthesis techniques. Alkylenebis(acrylamide)s and alkylenebis(methacrylamide)s can be made by treating the corresponding alkylenediamine with acryloyl chloride or methacryloyl chloride in dimethylformamide or water in the presence of an HCl sequestrant, e.g., pyridine.

Crosslinked copolymers of the present invention may optionally include monomeric units derived from a third monomer, wherein the third monomer is substituted for a portion of the first monomer. Suitable third monomers are those monomers which may be copolymerized with the first monomer and the second monomer. Compounds suitable as the third third monomer include, e.g., acrylamide, methacrylamide and ethylvinylbenzene.

Preferably, the copolymer of the present invention includes from more than 0.5 mole percent up to about 20.0 mole percent monomeric units derived from the crosslinking monomer. More preferably, from about 2.0 mole percent to about 8.0 mole percent of the monomeric units of the copolymer are derived from the crosslinking monomer.

In a highly preferred embodiment, the sequestrant of the present invention is the crosslinked reaction product of from more than 94.0 mole percent to 99.5 mole percent of a dimethylamino$(C_2-C_6)$alkylmethacrylamide and from 0.5 mole percent to less than 6.0 mole percent of a $(C_3-C_{12})$alkylene bis(methacrylamide).

In a very highly preferred embodiment, the sequestrant of the present invention comprises the crosslinked polymerization product of about 95.6 mole percent dimethylaminopropylmethacrylamide and about 4.4 mole percent N,N'-hexamethylenebis(methacrylamide).

The crosslinked polymeric particles formed by the above described methods are washed with deionized water to remove salt used in the reaction mixture, to remove unreacted monomer from the particles and to remove water extractable noncrosslinked polymer from the particles. The water extractable polymer is measured, e.g., by analysis of an aqueous extract of the polymeric particles by gel permeation chromatography as more fully described in Example 1 below.

The washed particles are then dried, e.g., at 40° to 60° C. under vacuum (preferably less than 1.0 millimeter of mercury) until dry.

In an alternative method, particles of a crosslinked polymeric matrix having reactive sites thereon are functionalized by reacting the reactive sites with an appropriate reactant to form polymeric branches on the crosslinked matrix.

In a preferred embodiment of the alternative method, divinylbenzene-crosslinked poly(methacrylic anhydride) particles are treated with excess amine, e.g., diethylenetriamine, triethylenetetraamine, dimethylaminopropylamine, dimethylaminobutylamine, oligomers of ethylenediamine, by heating a mixture of the particles in an aqueous solution of the amine. The sequestrant particles so formed are then washed, e.g., with a solution of water and alcohol, to remove substantially all residual amine from the particles.

Optionally, the particles made by either of the above described methods may be ground, e.g., in a high shear grinder, to produce particles having a desired mean particle diameter, e.g., from about 10 microns to about 400 microns.

Sequestrants of the present invention may be used in the form of free bases or in the form of pharmaceutically acceptable acid salts, i.e., salts whose anions are in therapeutically effective amounts nontoxic to the organism to whom the salts are administered.

Pharmaceutically acceptable salt forms of the sequestrant of the present invention include those derived from mineral acids, such as hydrochloric acid and phosphoric acid, or organic acids, such as acetic acid, citric acid, lactic acid and malonic acid. The salt forms of the sequestrant of the present invention may be prepared by dissolving the acid in a suitable solvent, e.g., water or a solution of water and an alcohol, treating the free base with the solution to form the salt and then isolating the insoluble salt from the solution.

The sequestrant of the present invention can be orally administered in any suitable way. The sequestrant may be administered, for example, in the form of tablets, capsules, or particles, i.e., granules or powder, or as an aqueous suspension. In the case of tablets for oral use, carriers which are commonly used including, e.g., lactose and corn starch, and lubricating agents, such as magnesium stearate, may be added. For oral administration in capsule form, useful diluents include, e.g., lactose and dried corn starch. When aqueous suspensions are required for oral use, the active ingredient is combined with emulsifying and suspending agents. If desired, sweetening and flavoring agents may be added. Particulate forms of the sequestrant administered as a mixture with a food item such as applesauce, stewed fruits, juices and cereals.

The dosage of the sequestrant of the present invention that will be most suitable will vary with the form of administration, the particular embodiment of sequestrant and the physiological characteristics of the host to which the sequestrant is administered. Based on physiological studies with beagle dogs, (described below in Example 14) the therapeutic dosage in humans will be from about 2 to about 125 milligrams per kilogram of body weight per day, i.e., about 0.2 grams to about 10 grams per day for an 80 kilogram host. It is expected that more widely used dosages will be from about 35 to about 50 milligrams per kilogram of body weight per day or about 2.5 to about 4 grams per day for an 80 kilogram host.

The sequestrants of the present invention can be used in combination with other treatments that are designed to lower the level of cholesterol in the blood. In a highly preferred embodiment, a sequestrant of the present invention is used in combination with a material that is effective in inhibiting biosynthesis of cholesterol. Examples of such agents would include but are not limited to HMG-CoA reductase inhibitors, HMG-CoA synthase inhibitors, and squalene epoxidase inhibitors and squalene synthase inhibitors. Illustrative of such HMG-CoA reductase inhibitors are lovastatin, simvastatin, pravastatin and fluvastatin. Examples of HMG-CoA synthase inhibitors are the beta-lactone derivatives disclosed in U.S. Pat. No. 4,806,564; 4,816,477; 4,848,271; and 4,751,237; the beta-lactam derivatives disclosed in U.S. Pat. Nos. 4,983,597 and 5,120,729; and the substituted oxacyclopropane analogues disclosed in European Patent Publication EP 0411703. Illustrative examples of squalene epoxidase inhibitors are disclosed in European Patent Publication EP. 0318860 and in Japanese Patent Publication J02169571A. Illustrative Examples of squalene synthase inhibitors are disclosed in European Patent Publication EP 05/2865. LDL-receptor gene inducer molecules are disclosed in EPO Publication 505135 published Sep. 23, 1992. Other cholesterol lowering agents that may be administered include niacin, probucol, the fibric acids (clofibrate and gemfibrozil) and LDL-receptor gene inducers.

EXAMPLE 1

Hexamethylenebis(methacrylamide), HMBMAM (27.7365 g of 87.11% purity by high performance liquid chromatography; 24.1613 g pure HMBMAM, 0.0957 mole) was added to dimethylaminopropylmethacrylamide, DMAPMAM (354.30 g of 99.50% purity by gas-liquid chromatography; 352.53 g, 2.071 mole pure DMAPMAM) in a beaker with stirring via a magnetic stirring bar, so that the mole % HMBMAM of the polymerizable monomers was 4.42. Some of the material added as HMBMAM remained undissolved after stirring for one hour. The insoluble material was most likely polymer which was the most probable impurity in the HMBMAM monomer.

A cellulosic dispersant 5.1271 g of Natrosol Plus HEC 330 Grade from Aqualon, Wilmington, Del.), sodium lauryl sulfate (1.7104 g), and anhydrous sodium sulfate (340.20 g, 2.395 mole) were combined and ground together in a mortar. The resultant dry powder was dissolved by gradual addition over thirty minutes into 2412.2 g of deionized water (133.90 moles) in a five liter, four-necked round-bottomed reaction flask with stirring. The reaction flask was equipped with a stirrer bearing, a metal stirring shaft (316 stainless steel) fitted at the bottom end with a crescent-shaped teflon paddle, an addition funnel, a thermowell fitted with a temperature sensing probe, and a Claisen adaptor carrying a Friedricks condenser on one opening and a gas inlet fitting for nitrogen introduction on the other opening. The Friedricks condenser was cooled with an aqueous glycol liquid which was cooled to about $-10°$ C. with a refrigeration unit. An additional 108 g of deionized water $H_2O$ (5.995 moles) was used to rinse the mortar free of solid powder. The temperature sensing probe was connected to a microprocessor which regulates the temperature profile during the reaction.

The liquid mixture of monomers, HMBMAM and DMAPMAM, was transferred into the reaction flask with stirring, and deionized water (550.0 g, 30.53 moles) was used to rinse the beaker in order to complete the transfer of monomers. The total quantity of deionized water in the reaction flask was 3070.2 g (170.42 moles).

Sparging of the liquid by nitrogen was begun to free the system of oxygen while the mixture was heated to 72° C. at a rate of 1.0°/minute. After the liquid mixture, which was cloudy, reached 72° C., the nitrogen sparging was continued for another 30 minutes. The sparging was changed to a sweeping of the vapor space by a much slower rate of nitrogen flow, and a solution of 2.5928 g (0.01044 mole) 2,2-azobis(2,4-dimethylvaleronitrile) (Vazo 52, DuPont) and 1.0523 g (0.005473 mole) 2,2'-azobis(2-methylbutanenitrile) (Vazo 67, DuPont) in 7.0508 g of acetone was introduced quickly into the reaction flask so as to allow no entry of oxygen. The reaction mixture was held at 72° C. for 2.5 hours following introduction of the initiators. Following the 2.5 hours at 72° C., the temperature was increased from 72° C. to 90° C. at a rate of 1.0° C. per min., held at 90° C. for 3.0 hours, then raised to 100° C. for 3.0 hours. Almost immediately with the addition of the initiators, a precipitate of small solid particles began to form. Precipitation of the growing crosslinked polymer continued until all the monomers were depleted from the aqueous phase. This time-temperature profile completely decomposed all the initiator so that the final polymer product has an undetectable level by high performance liquid chromatography at a detection limit of 0.1 ppm. On standing the slurry separated into two layers, i.e., a top layer of polymer particles and a bottom layer of clear liquid.

The slurry of fine particles with diameters of 50 to about 400 microns was cooled to ambient temperature and washed seven times with deionized water. Each washing was performed by adding 2500 g of deionized water, stirring the aqueous slurry for 15 minutes, and siphoning off the liquid. Each siphonate was assessed for clarity and the presence of sulfate anion by treatment with barium chloride solution. Siphonates one through three (not including the mother liquid siphonate) were cloudy and tested positive for sulfate anion. Siphonates four through six tested positive for sulfate anion but were clear. Siphonate seven was clear and free of sulfate anion. An eighth washing was done with 2000 g of deionized water. The slurry was stirred for 15 minutes, filtered through a Büchner funnel, and drained free of bulk water via vacuum suction of air through the bed of solid particles. A total of 19,500 g of deionized water were used to wash the polymer. The hydrated solid weighing 1384.2 g was dried for 16 hours at 65° C. in a convection oven and gave 340.9 g of air-dried product which on further drying in a vacuum oven gave 328.18 g. Counting the polymer weight from two samples thieved for solids measurements gave a total yield of vacuum dried polymer of 329.83 g which represents an 86.01% yield of theory.

An aqueous extraction of the dried polymer gave a peak in a gel permeation chromatograph indicating that a small amount of linear polymer was still present in the product. A slurry of 48.1 g of the dry polymer in 3000 g of deionized water was agitated for an hour and then allowed to sit overnight. The polymer was isolated by siphoning off the liquid; an aqueous extract of this polymer was found to contain no linear polymer at the limit of detection of about one part per hundred.

All the synthesis procedures listed as that of Example 1 in Table 1 below followed the description given here except that the use of sodium lauryl sulfate was dropped from some of them as noted in Table 1. The sodium lauryl sulfate was found to contribute nothing to regulation of the grain size of the growing precipitated polymer but did make the washing steps more difficult by producing foam and was therefore eliminated from subsequent runs.

The particles so formed were ground in a high shear grinder (a coffee grinder) for 30 seconds so that the ground particles, when hydrated, exhibited a particle size distribution wherein 10% of the particles exhibited a mean particle size of less than 41 microns, 50% of the particles exhibited a mean particle size of less than 171 microns and 90% of the particles exhibited a particle size of less than 370 microns.

EXAMPLE 2

Ethylenebis(acrylamide), EBAM (11.0166 g of 80.9% purity by gas-liquid chromatography; 8.9124 g pure EBAM, 0.05299 mole or 3.00 mole % of the polymerizable monomers) was mixed with dimethylaminopropylmethacrylamide, DMAPMAM (292.67 g of 99.67% purity by gas-liquid chromatography; 291.31 g, 1.7110 moles of pure DMAPMAM or 97.00 mole % of the polymerizable monomers) in a beaker with stirring to give a clear solution free of suspended solid.

A cellulosic dispersant, (4.0508 g of Natrosol Plus HEC, Grade 330, Aqualon, Wilmington, Del.) and 270.0 g (1.90 moles) anhydrous sodium sulfate were ground together in a mortar and pestle to give a finely divided white powder. The white powder was added with stirring to deionized water (2328.7 g; 129.26 moles) in a five liter, four-necked round-bottomed reaction flask over thirty minutes to give a liquid phase that is slightly cloudy but homogenous.

The reaction flask was equipped with a stirrer bearing, a metal stirring shaft (316 stainless steel) fitted with a crescent shaped teflon paddle, an additional funnel, a thermowell fitted with a temperature sensing probe connected to a microprocessor for controlling the time-temperature profile, and a Claisen adaptor carrying a Friedricks condenser and an inlet for nitrogen gas. The nitrogen gas was used to deoxygenate the contents of the reactor, and the Friedricks condenser was cooled with an aqueous glycol liquid which was cooled to about −10° C. with a refrigeration unit.

The liquid mixture of EBAM and DMAPMAM monomers was transferred to the reaction flask, and the beaker containing the liquid monomers was flushed with 44.5 g (24.67 moles) of deionized water to complete the transfer to the reactor. The total water quantity in the reactor was 2424.6 (134.58 moles).

The liquid mixture was heated to 72° C. at a programmed heat up rate of 1.0° C./min. with stirring and sparging by nitrogen to free the system of oxygen. At 72° C. a slow nitrogen sparge was continued for 25 minutes to complete the removal of oxygen. The nitrogen sparge was changed to a slow sweep by nitrogen through the vapor space of the reactor, and two initiators, 2.1023 g, (0.008464 mole, 0.004798 mole per mole of monomers) of 2,2-azobis(2,4-dimethyl-valeronitrile), Vazo 52, DuPont and 0.8244 g, (0.004288 mole, 0.002431 mole per mole of monomers) of 2,2′-azobis(2-methybutanenitrile), Vazo 67, DuPont, dissolved in 7.0 grams of acetone were added to the reaction mixture all at once. A finely divided solid of polymer began to precipitate within five minutes of introduction of the initiators. The reaction mixture was stirred at 72° C. under a nitrogen atmosphere for 2.5 hours after which the temperature was ramped to 90° C. at a rate of 1.0° C. per minute (18 minutes duration). The mixture or slurry was stirred at 90° C. for 3.0 hours, followed by a temperature ramp to 100° C. at a rate of 1.0° C./minute (10 minutes duration), and held at 100° C. for 3 hours. This three tier, temperature-time profile with the intervening ramps was sufficient to decompose both initiators completely so that there was no measurable trace of initiators in the final, washed polymer particles at a limit of detection of 1 ppm via high perfomance liquid chromatography.

The cooled slurry at ambient temperature separated into two layers, i.e., a top layer of slurry of polymer particles and a bottom layer of clear aqueous salt solution. A microscopic view of the particles of polymer indicated a particle size range of about 50 to 300 microns diameter. The bottom layer was siphoned off, and the solid particles were washed seven times with an average of 3,133 g of deionized water per washing. Each washing was carried out by stirring the particles in a fresh quantity of deionized water for about 30 minutes followed by siphoning of the aqueous wash liquor while stirring the particle slurry. Five washings required an eight hour day. As the salt concentration diminished in the liquid phase of the slurry, the polymer particles swelled and the volume of particles increased. The volume increase was directly related to the level of crosslinking monomer within the polymer particle.

The wash liquors from the first four siphoning were cloudy; the fifth wash liquor was clear; and the seventh was the first liquor to give no positive test for sulfate anion on treatment by barium chloride solution. Following the seventh washing, the particles were slurried in 1500 g of deionized water for about thirty minutes and isolated on a Büchner funnel. The total weight of liquor from the washings was 22,822.2 g. The hydrated solid weight of polymer particles was 2337.48 g; the dry polymer weight was 330.0 g after drying 16 hours at 60° C. in a convection oven. The measured solids on the dried polymer particles was 87.70%, so that the yield of anhydrous polymer was 289.4 g or 94.63% of the theoretical yield (based upon 305.85 g theory). The physical properties and measured efficacy for this polymer are provided in the tables.

The particles so formed were ground in a high shear grinder (a coffee grinder) for 30 seconds so that the ground particles, when hydrated, exhibited a particle size distribution wherein 10% of the particles exhibited a mean particle size of less than 37 microns, 50% of the particles exhibited a mean particle size distribution of less than 240 microns and 90% of the particles exhibited a mean particle size of less than 444 microns.

EXAMPLE 3

Hexamethylenebis(methacrylamide), HMBMAM, (25.5854 g. of 87.1% purity by high perfomance liquid chromatography; 22.285 g. pure HMBMAM, 0.0883 mole) was added to dimethylaminopropylmethacrylamide, DMAPMAM, (326.02 g. of 99.67% purity by gas-liquid chromatography; 324.9 g., 1.908 moles pure DMAPMAM) in a beaker with stirring via a magnetic stirring bar. Some of the material added as HMBMAM remained undissolved after stirring for more than one hour. The insoluble material was most likely polymer which was the most probable impurity in the HMBMAM monomer.

A cellulosic dispersant (4.7212 g. of Natrosol Plus HMHEC 330 Grade) and sodium sulfate (314.6 g., 9.98 wt. % of the aqueous phase) were combined and ground together in a mortar. The resultant mixture was added to deionized water 2123.5 g.) in a five liter, four-necked round-bottomed reaction flask over a thirty minute period with stirring. The reaction flask was equipped with a stirrer bearing a metal stirring shaft (316 stainless steel) fitted with a crescent shaped teflon paddle, an addition funnel, a thermowell fitted with a temperature sensing probe, and a Claisen adaptor carrying a Friedricks condenser. The Friedricks condenser was cooled with an aqueous glycol liquid which was cooled to about −10° C. with a refrigeration unit. The temperature sensing probe was connected to a microprocessor which regulated the temperature profile during the reaction.

The liquid mixture of HMBMAM and DMAPMAM was transferred to the reaction flask, and deionized water (708.0 g) was used to complete the transfer of undissolved HMBMAM.

The reaction mixture was heated to 72° C. at a rate of 1° C./min. with stirring and sparging by nitrogen to free the system of oxygen. At 72° C. the liquid was sparged for another 35 minutes to complete the removal of oxygen. The nitrogen sparge was changed to a slow sweep and the initiator dissolved in acetone (2.4025 g., 0.009673 mole of 2,2-azobis(2,4-dimethylvaleronitrile) in five grams of acetone) was charged to the reaction flask. The reaction mixture was stirred at 72° C. for 2.5 hours following the introduction of the initiator; the temperature then was increased from 72° to 90° C. at a rate of 1° C./minute, and the mixture of finely divided solid in liquid was held at 90° for three hours. Very shortly after the initiator was charged, a precipitate began to form as small grainy material until all the monomer had polymerized. Upon completion of the temperature profile, the slurry of small particles (particle diameter of 50 to 300 microns) was allowed to cool to ambient temperature. On standing, the slurry separated into two layers, i.e., a top layer of slurry and a clear bottom layer of aqueous salt solution.

The bottom liquid layer was siphoned off, and the remaining solid particles were washed ten times with 2500 gram aliquots of deionized water per washing treatment. The seventh washing liquor tested free of sulfate ion via a barium sulfate test and was clear without a haze. The wash liquors one through five were decreasing in cloudiness or haze but tested positive for sulfate ion. Liquor from wash number six was clear but contained traces of sulfate ion. Liquor from wash number seven was clear and free of sulfate ion.

The yield of dried polymer was 332.7 g. or 94.05% of theory (including the weight of initiator fragments and the dry weight of a sample removed during processing).

EXAMPLE 4

The experimental procedure for Example 4 is identical to that of Example 2 except that the time-temperature profile did not have the third tier at 100° C. for 3 hours. The synthesis procedure had only two temperature plateaus; one at 72° C. for 2.5 hours and a second at 90° C. for 3 hours.

EXAMPLES 5-23

The sequestrants of Examples 5 to 21 were each made by one of the methods set forth above in Examples 1 to 4, as noted in below in Table 1, except that the composition and/or relative amount of crosslinking monomer was changed as noted in Table 1. The following crosslinking monomers were used: divinylbenzene (DVB), N,N′-methylenebis(acrylamide) (MBAM), N,N′-methylenebis-(methacrylamide) (MBMAM), N,N′-ethylenebis(acrylamide) (EBAM), N,N′-hexanethylenebis(methacrylamide) (HMBMAM), N,N′-octamethylenebis(acrylamide) (OMBAM) and N,N′-dodecamethylenebis(acrylamide) (DDMBAM). The DVB monomer included ethylvinylbenzene (EVB) as an impurity and the mole % EVB in each of the DVB-crosslinked sequestrants is noted in Table 1 in parentheses following the mole % DVB.

TABLE 1

| Ex. No. | Method (Ex. No.) | Crosslinking Monomer | Mole % Crosslinking Monomer |
| --- | --- | --- | --- |
| 5 | 2* | DVB (EVB) | 0.99 (0.074) |
| 6 | 2* | DVB (EVB) | 2.99 (0.223) |
| 7 | 2* | DVB (EVB) | 5.00 (0.38) |
| 8 | 3 | MBMA | 5.0 |
| 9 | 3 | MBMA | 10.1 |
| 10 | 2 | MBMAM | 0.94 |
| 11 | 2 | MBMAM | 2.03 |
| 12 | 3 | MBMAM | 2.03 |
| 13 | 2* | EBAM | 0.99 |
| 14 | 2 | EBAM | 1.99 |
| 16 | 1 | HBMAM | 0.88 |
| 17 | 1 | HBMAM | 1.77 |
| 18 | 1 | HBMAM | 2.65 |
| 19 | 2* | HBMAM | 3.47 |
| 20 | 3 | HBMAM | 4.39 |
| 21 | 1* | HBMAM | 4.40 |
| 22 | 2 | OMBAM | 5.0 |
| 23 | 2 | DDMBAM | 5.0 |

*No sodium lauryl sulfate in aqueous phase

EXAMPLE 24

An aqueous solution was prepared. Sodium chloride (300 g) was dissolved in 1350 g deionized water at 50° C. and 57.57 g sodium chloride was ground with 5.4 g of a cellulosic dispersant (Natrosol Plus HEC Type 330, Aqualon Inc.) in a mortar to form a homogeneous mixture. The ground mixture was then slowly added to the salt solution and stirred at 50° C. until all the solids had dissolved.

An organic mixture was prepared by mixing 222.24 g dimethylamino-propylmethacrylamide, 11.76 g high purity (80% pure) divinylbenzene, 1.18 g diethyleneglycol divinyl ether, 214.83 g o-xylene and 2.335 g 2,2′-azobis-(2,4-dimethylvaleronitrile) (Vazo 52, DuPont).

The aqueous mixture was placed in a reaction vessel and stirred at 52° C. The organic mixture was added to the reaction vessel, stirring at 52° C. was continued for 20 hours, resulting in formation of spherical particles.

The particles were washed with deionized water to remove the salt and most of the o-xylene. The remaining xylene was stripped from the particles at 102° C. using a steam sweep distillation.

EXAMPLE 25

Particles of a divinylbenzene and methacrylic anhydride copolymer were made by the procedure set forth below.

An aqueous solution was prepared by dissolving 0.889 g of a cellulosic dispersant (Culminal CMMC-2000) and 0.059 g sodium lauryl sulfate in 591.644 g deionized water.

An organic mixture was made by dissolving 0.691 g 75% alpha-cumyl peroxyneodecanoate in odorless mineral spirits (Lupersol 188 M75) and 1.037 g di(4-tert-butylcyclohexyl)peroxydicarbonate (Percadox 16N) in a mixture of 32.997 g methacrylic anhydride, 18.855 g divinylbenzene (55% purity) and 22.22 g isooctane.

The aqueous solution was charged to a 1 liter round bottomed flask equipped with a condensor, an agitator and a thermocouple. The organic mixture was added to the aqueous solution. The organic mixture and aqueous solution were agitated to disperse the organic mixture in the aqueous solution and then heated from 25° C. to 60° C. at 0.5° C. per minute. The dispersion was then held at 60° with continued agitation for 20 hours to form spherical copolymeric particles having a mean particle size of 175 microns.

The copolymeric particles were then functionalized with dimethylaminopropylamine. Dimethylaminopropylamine (43.833 g) was dissolved in approximately 500 g deionized water. Wet copolymeric particles (39.03 g dry weight) were added to the aqueous solution. The mixture was stirred while the temperature was increased from 22° C. to 50° C. at the rate of 1° C. per minute and held at 50° C. for 5 hours. The mixture was allowed to cool, and the particles were separated from the liquid and washed with a methanol/water (50/50) solution.

EXAMPLE 26

Divinylbenzene-crosslinked poly(methacrylic anhydride) particles made by the method set forth above in Example 25 were functionalized by treating the particles with triethylenetetraamine (TETA).

TETA (292.48 g) was dissolved in about 300 g deionized water. The divinylbenzene-crosslinked poly(methacrylic anhydride) particles (120 g) were then added to the aqueous solution at 40° C. The mixture was then stirred while the temperature was increased from 40° C. to 95° C. at a rate of 1° C. per minute and then held at 95° C. for 5 hours to produce the TETA-functionalized particles. The mixture was allowed to cool, and the particles were washed sequentially with water and then methanol to rinse the particles free of residual amine. The particles so formed exhibited a mean particle size of 145 microns.

EXAMPLE 27

Elemental analyses for several of the above described exemplary sequestrants are set forth below in Table 2.

TABLE 2

| Ex. No. | % Carbon | % Hydrogen | % Nitrogen | % Oxygen |
|---|---|---|---|---|
| 1 | 60.835 | 10.610 | 15.555 | 12.820 |
| 7 | 60.190 | 10.550 | 14.900 | 13.515 |
| 8 | 57.530 | 10.420 | 15.095 | 15.040 |
| 12 | 58.740 | 10.480 | 15.445 | 14.890 |
| 17 | 61.63 | 10.595 | 15.885 | 12.035 |
| 18 | 61.055 | 10.565 | 14.385 | 12.800 |
| 19 | 58.710 | 10.600 | 14.795 | 15.620 |
| 21 | 62.890 | 10.645 | 15.985 | 11.685 |
| 25 | 61.6 | 8.61 | 5.45 | 24.34 |

The amount of water extractable linear polymer residue in several of the above described exemplary sequestrants was determined by analyzing an aqueous extract of the crosslinked polymer particles by gel permeation chromatography.

An aqueous extract was prepared by shaking a mixture of crosslinked particles in an aqueous solution of 0.1 m $Na_2SO_4$, 1% acetic acid and 5 ppm of a biocide (Kathon 866) at room temperature for one hour and filtering the mixture through an 0.45 μm membrane filter (Millipore). The mixture included about 50 mg (dry weight) crosslinked particles/1 ml aqueous solution.

The filtrate was analyzed by gel permeation chromatography using a 4 cm×6 mm ID guard column (PWXL Progel, TSK guard column, Supelco, Inc.), a 30 cm×7.8 mm ID column (G3000 PWXL, Progel TSK column, Supelco, Inc.), a pump (Waters 501) with variable volume autosampler (Spectra Physis AS 300); and a refractive index detector (Perkin Elmer LC 30).

The above described aqueous extract was used as the mobile phase and the system was operated using a 50 μl loop injection, a column temperature of 30° C. and an analysis time of 23 minutes.

The response peaks were integrated from 4.75 minutes to 9.2 minutes and the amount of linear polymer in the sample extract was determined by comparison with results obtained with aqueous poly(dimethylaminopropylmethacrylamide) solutions of known concentration.

The percent linear polymer present in the crosslinked particulate sample was calculated according to Equation(1):

$$\text{Weight \% Linear polymer} = \frac{\left(\begin{array}{c}\text{Linear polymer}\\\text{In Extract (mg/ml)}\end{array}\right)\left(\begin{array}{c}\text{Mobile Phase}\\\text{In Extract (ml)}\end{array}\right)(100)}{\left(\begin{array}{c}\text{Dry Weight of Crosslinked}\\\text{Particles Extracted (mg)}\end{array}\right)} \quad (1)$$

Comparison of peak retention times for the linear polymer to the poly(dimethylaminopropylmethacrylamide) standard also indicated that the linear polymer present had a MW of less than about 50,000.

The moisture holding capacity of several of the above described exemplary sequestrants were determined by;
a) hydrating a quantity of the sequestrant by immersion in deionized water for at least 30 minutes;
b) filtering the hydrated quantity of sequestrant through medium porosity filter paper in a Büchner funnel under a vacuum of about 700 mm Hg for 5 minutes to dewater the sequestrant;
c) weighing a 3 to 5 gram sample of the dewatered sequestrant to the nearest 0.001 gram;
d) drying the sample at a temperature of 100° C. to 110° C. for at least 16 hours;
e) weighing the dried sample to the nearest 0.001 gram; and
f) calculating the moisture holding capacity of the sequestrant according to Equation (2):

$$\text{Moisture Holding Capacity (\%)} = \frac{(\text{Weight of dewatered sample} - \text{Weight of dried sample})}{(\text{Weight of dewatered sample})} \quad (2)$$

The moisture holding capacity, expressed as a percentage of the weight of dewatered hydrated sequestrant (%) as calculated by equation 1, the anion exchange capacity, expressed in milliequivalents per gram sequestrant (meq/g) and the amount of water extractable polymer, expressed as a percentage of the weight of sequestrant particles extracted (%) as calculated by equation 2, of several of the above described exemplary sequestrants are set forth below in Table 3.

TABLE 3

| Ex. No. | Moisture Holding Capacity (%) | Anion Exchange Capacity (meq/g) | Extractable Polymer (wt %) |
|---|---|---|---|
| 1 | 84.26 | 5.44 | 0.4520 |
| 2 | 87.76 | 5.64 | 0.3550 |
| 3 | 70.10 | 5.59 | 0.367 |
| 4 | 96.16 | 5.93 | 0.9212 |
| 5 | — | — | 0.6624 |
| 6 | 72.20 | 5.55 | — |
| 7 | 77.39 | 5.37 | 0.3886 |
| 8 | 76.49 | 5.54 | 0.1857 |
| 9 | — | — | — |
| 10 | 91.52 | 5.62 | 2.0408 |
| 11 | 72.69 | 5.73 | 1.0850 |
| 12 | 76.74 | 5.38 | 0.0981 |
| 13 | 94.29 | — | 0.9296 |
| 14 | 90.70 | — | 0.6678 |
| 15 | 81.05 | 5.67 | 0.2058 |
| 16 | 91.46 | 5.51 | 0.5825 |
| 17 | 84.72 | 5.63 | 1.3389 |
| 18 | 82.98 | 5.38 | 0.6958 |
| 19 | — | 5.80 | 1.35 |
| 20 | 70.70 | 5.44 | 0.3192 |
| 21 | 72.12 | — | — |
| 25 | 24.07 | — | — |

EXAMPLE 28

The efficacy of the crosslinked copolymer of the present invention is a bile acid sequestrant was evaluated in beagle dogs.

Beagle dogs weighing 9 to 11 kg each were fed a semi-synthetic, low cholesterol diet once per day in a quantity (200 to 300 grams/dog/day) that stabilized the body weight of the respective dogs.

The semi-synthetic diet included 32.01% vitamin free casein; 43.14% dextrose; 12.42% lard; 2.39% cod liver oil; 2.72% calcium phosphate; 4.92% cella flour; and 2.39% hegsted vitamin mix No. 14.

Baseline plasma cholesterol levels were assessed for each dog by feeding the semi-synthetic diet without a bile acid sequestrant for six months and measuring plasma cholesterol levels on blood samples taken twice per week.

After the baseline serum cholesterol levels were established, cholestyramine bile acid sequestrant was mixed with the diet (at dosages of 3, 6 and 12 grams/dog/day) plasma cholesterol levels were measured twice a week for four weeks to characterize the relationship between cholestyramine dosage and serum cholesterol levels for each dog.

Following derivatization of the dose/response relationship, the dogs were maintained on a regimen of 12 grams cholestyramine/dog/day until a copolymer of the present invention was substituted for the cholestyramine in the diet at a dosage of either 3 g/dog/day or 6 g/dog/day. The dogs were fed the copolymer of the present invention and the plasma cholesterol levels of the dogs were measured daily for four weeks.

The serum cholesterol level of dog fed a bile acid sequestrant stabilizes at a level below to baseline level. The relative efficacy of the crosslinked copolymeric bile acid sequestrant of the present invention and of a control dosage of 12 g cholestyramine/day was quantified by calculating an efficacy factor ("EF") according to Equation (3):

$$EF = \left(\frac{N-B}{N-A}\right)\left(\frac{12}{X}\right); \quad (3)$$

wherein:
EF = efficacy factor
N = serum cholesterol level in milligrams cholesterol/deciliter serum (mg/dl) on the semi-synthetic diet without a bile acid sequestrant,
A = serum cholesterol level (mg/dl) or semi-synthetic diet including 12 g cholestyramine/day;
X = (grams dosage of bile acid sequestrant of the present invention as bile acid sequestrant of the present invention/day) included in serum synthetic diet, and;
B = serum cholesterol level (mg/dl) on semi-synthetic diet including X grams of crosslinked copolymeric bile acid sequestrant of the present invention.

The sequestrants of Examples 1 to 26 and Comparative Example C1 (poly(dimethylaminopropylmethacrylamide) having a number average molecular weight of 261,200, and a weight average molecular weight of 588,400 and a molecular weight mode of 477,000) were each tested in beagle dogs according to the above method. Results are set forth below in Table 4 as the EF, calculated according to equation 3, for each of the sequestrants tested, along with the dosage administered, expressed as grams sequestrant per dog per day (g/dog/day) and a number (Dog No.) identifying the dog to which the dosage was administered.

TABLE 4

| Ex. No. | Dog No. | Dosage (g/dog/day) | EF |
|---|---|---|---|
| 1 | 303 | 6 | 1.6 |
| 1 | 207 | 3 | 5.13 |
| 2 | 91 | 6 | 3.6 |
| 3 | — | 3 | 4.0 |
| 4 | 302 | 6 | 2.78 |
| 5 | 209 | 3 | 1.33 |
| 5 | 302 | 6 | 1.8 |
| 6 | 206 | 3 | 1.7 |
| 6 | 203 | 6 | 1.9 |
| 7 | 205 | 3 | 2.06 |
| 7 | 94 | 6 | 2.29 |
| 7 | 207 | 3 | 3.04 |
| 8 | 305 | 6 | 2.2 |
| 9 | 303 | 3 | 1.3 |
| 10 | 300 | 6 | 4.38 |
| 11 | 202 | 6 | 1.2 |
| 12 | 212 | 6 | 2.98 |
| 13 | 92 | 6 | 2.29 |
| 14 | 201 | 6 | 2.1 |
| 15 | 203 | 6 | 2.89 |
| 16 | 209 | 6 | 3.82 |
| 17 | 305 | 6 | 2.2 |
| 18 | 304 | 6 | 2.4 |
| 19 | 207 | 3 | 4.6 |
| 20 | 204 | 6 | 2.94 |
| 20 | 206 | 3 | 5.20 |
| 21 | 201 | 6 | 3.8 |
| 21 | 305 | 3 | 4.4 |
| 21 | 212 | 3 | 4.51 |
| 24 | 207 | 6 | 1.34 |
| 22 | 209 | 3 | 2.14 |
| 23 | 301 | 3 | 2.67 |
| C1 | 206 | 6 | 3.17 |
| C1 | 207 | 6 | 3.34 |
| 26 | 204 | 3 | 1.55 |

EXAMPLE 29

A suspension of particles of the sequestrant in deionized water was prepared. The suspension was serially diluted into serumless culture medium. The most concentrated suspension tested was 1000 micrograms sequestrant per milliliter suspension (μg/ml).

Exponentially growing Chinese hamster ovary (CHO) cell cultures were treated with the sequestrant dilutions for three hours. The cultures were gently rocked on a rocker platform during treatment in an attempt to maintain a uniform suspension over the cells for the entire treatment period. Negative controls i.e., CHO cell cultures treated with serumless culture medium, and solvent controls, i.e., CHO cell cultures treated with 1% deionized water in serumless culture medium, were included.

Treatment was terminated by washing the cultures twice with Dulbecco's phosphate buffered saline and cells were allowed to recover in McCoy's 5A medium containing 10% fetal bovine serum for 0, 5 or 21 hours, i.e., 3, 8 or 24 hours from the beginning of treatment.

Cells were harvested at 3 and 24 hours by treating with trypsin-EDTA and scraping the cell monolayers from the culture flasks. The harvested cells were counted by Coulter counter to determine relative reductions in cell numbers. At selected doses, Trypan blue exclusion counts were conducted using a hemacytometer to determine cell viability to control for the possibility that some dead cells may have been counted with the Coulter counter. No cell counts were conducted at 8 hours, but the culture monolayers were examined for evidence of toxicity under an inverted microscope.

The sequestrants of Examples 4, 15 and 20 and comparative Example C1 (described above in Example 28) were each tested for cytotoxicity using the procedure set forth above.

The results of cytotoxicity testing is set forth below in Table 5 as an $ED_{50}$ value in μg/ml for each sequestrant tested, wherein the $ED_{50}$ values indicate the dosage of the respective sequestrant effective to kill 50% of the cells in the cell culture treated.

TABLE 5

| Example No. | $ED_{50}$ (μg/ml) |
|---|---|
| 4 | 700 |
| 15 | >1000 |
| 20 | 500 |
| C1 | 10.0 |

EXAMPLE 30

As a specific embodiment of an oral composition of a compound of this invention, 1 g of the compound from Example 1 is formulated with sufficient finely divided lactose to fill an appropriately sized hard gelatin capsule.

What is claimed:

1. A bile acid sequestrant, comprising:
a crosslinked polymeric matrix, comprising elongated matrix elements and an effective amount of crosslink matrix elements crosslinked with the elongated matrix elements to render said sequestrant insoluble in water, and
branch elements attached to the elongated matrix elements, said elongated matrix elements and attached branch elements being formed by polymeric chains of repeating units, said chains including units having the structural formula:

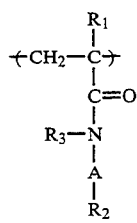

wherein
$R_1$ is H, $(C_1-C_8)$alkyl;
A is

or

$R_2$ is

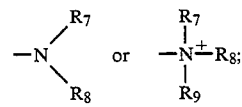

each occurrence of $R_3$, $R_4$, $R_5$, $R_6$, $R_7$, $R_8$, and $R_9$ is independently selected from the group consisting of H and $(C_1-C_8)$alkyl;
a is an integer from 1 to 20;
b is an integer from 1 to 10;
d is an integer from 1 to 10; and
e is an integer from 1 to 5;
and wherein the crosslink matrix elements comprise crosslink matrix elements having the structural formula:

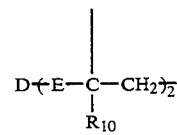

or

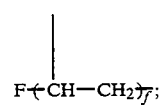

wherein
D is

or

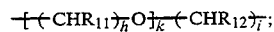

E is

—O—

-continued
or

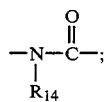

F is phenylene, (C$_1$-C$_4$)alkylphenylene or benzenetriyl;

each occurrence of R$_{10}$, R$_{11}$, R$_{12}$, and R$_{14}$ is independently selected from the group consisting of H and (C$_1$-C$_8$)alkyl; and f is 2 if F is phenylene or (C$_1$-C$_4$)alkylphenylene, and f is 3 if F is benzenetriyl;

g is an integer from 1 to 20;

h is an integer from 1 to 10;

i is an integer from 1 to 10; and j is an integer from 1 to 5;

and pharmaceutically acceptable salts thereof;

said sequestrant including less than 1.0 percent by weight water extractable polymer.

2. The sequestrant of claim 1, wherein:

R$_1$ is H or methyl;

A is —CHR$_4$)$_a$;

R$_2$ is

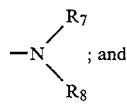

R$_4$ is H;

R$_7$ and R$_8$ are each methyl;

a is an integer from 2 to 6;

the crosslink elements have the structural formula:

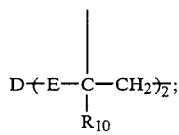

wherein
E is

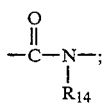

R$_{10}$ is H or methyl;

R$_{11}$ and R$_{14}$ are each H; and g is an integer from 1 to 12.

3. The sequestrant of claim 2, wherein a is 3 and g is 6.

4. The sequestrant of claim 1, wherein the crosslink elements have the structural formula:

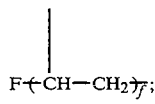

wherein
F is phenylene; and f is 2.

5. The sequestrant of claim 1, wherein the crosslinked polymeric matrix is in particulate form.

6. The sequestrant of claim 1, wherein the sequestrant has a mean particle diameter from about 10 microns and about 400 microns.

7. The sequestrant of claim 1, wherein the sequestrant has an anion exchange capacity from about 5 milliequivalents per gram and about 6 milliequivalents per gram.

8. The sequestrant of claim 1, wherein the sequestrant has a moisture holding capacity from about 70 weight percent to about 97 weight percent of fully hydrated sequestrant.

9. A bile acid sequestrant, comprising:

the crosslinked polymerization product of a mixture of a first monomer, said first monomer having the structural formula:

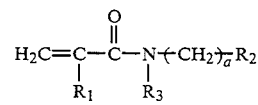

wherein
R$_2$ is

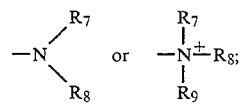

R$_1$, R$_3$, R$_7$, R$_8$ and R$_9$ are each independently H or (C$_1$-C$_8$)alkyl; and a is an integer between 1 and 20;

and a second monomer, said second monomer having the structural formula:

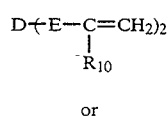

or

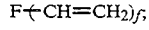

wherein
D is

or

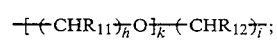

E is

—O— or

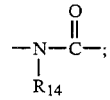

F is phenylene, (C$_1$-C$_4$)alkylphenylene or benzenetriyl;

each occurrence of $R_{10}$, $R_{11}$, $R_{12}$, and $R_{14}$ is independently selected from the group consisting of H and $(C_1-C_8)$alkyl; and f is 2 if F is phenylene or $(C_1-C_4)$alkylphenylene, and f is 3 if F is benzenetriyl;

g is an integer from 1 to 20;

h is an integer from 1 to 10;

i is an integer from 1 to 10; and j is an integer from 1 to 5;

and pharmaceutically acceptable salts thereof;

said sequestrant including less than 1.0 percent by weight water extractable polymer.

10. The sequestrant of claim 9, wherein the first monomer comprises a $di(C_1-C_8)$alkylamino$(C_1-C_{20})$alkylacrylamide or a $di(C_1-C_8)$alkylamino$(C_1-C_{20})$alkylmethacrylamide.

11. The sequestrant of claim 10, wherein the first monomer is selected from the group consisting of dimethylaminoethylacrylamide, dimethylaminoethylmethacrylamide, dimethylaminopropylacrylamide, dimethylaminopropylmethacrylamide, dimethylaminobutylacrylamide, dimethylaminobutylmethacrylamide dimethylaminopentylacrylamide, dimethylaminopentylmethacrylamide, dimethylaminohexylacrylamide, dimethylaminohexylmethacrylamide and mixtures thereof.

12. The sequestrant of claim 11 wherein the first monomer is dimethylaminopropylmethacrylamide.

13. The sequestrant of claim 9, wherein the second monomer comprises a $(C_1-C_{20})$alkylenebis(acrylamide) or a $(C_1-C_{20})$alkylenebis(methacrylamide).

14. The sequestrant of claim 13, wherein the second monomer comprises a $(C_1-C_{12})$alkylenebis(acrylamide) or a $(C_1-C_{12})$alkylenebis(methacrylamide).

15. The sequestrant of claim 14, wherein the second monomer is selected from the group consisting of N,N'-propylenebis(acrylamide), N,N'-butylenebis(acrylamide), N,N'-pentamethylene(bisacrylamide), N,N'-hexamethylenebis(acrylamide), N,N'-heptamethylenebis(acrylamide), N,N'-octamethylenebis(acrylamide), N,N'-decamethylenebis(acrylamide), N,N'-dodecamethylenebis(acrylamide), N,N'-propylenebis(methacrylamide), N,N'-butylenebis(methacrylamide), N,N'-pentamethylene(bismethacrylamide), N,N'-hexamethylenebis(methacrylamide), N,N'-heptamethylenebis(methacrylamide), N,N'-octamethylenebis(methacrylamide), N,N'-decamethylenebis-(methacrylamide), N,N'-dodecamethylenebis(methacrylamide), and mixtures thereof.

16. The sequestrant of claim 15, wherein the second monomer is N,N'-hexamethylenebis(methacrylamide).

17. The sequestrant of claim 9, wherein the second monomer comprise divinylbenzene.

18. The sequestrant of claim 9, wherein the sequestrant is the polymerized product of a mixture of the first monomer and from about 0.5 mole percent to about 20 mole percent of the second monomer.

19. The sequestrant of claim 9, wherein the sequestrant is the polymerized product of a mixture of the first monomer and from about 2 mole percent to about 8 mole percent of the second monomer.

20. The sequestrant of claim 9, wherein the sequestrant is the polymerized product of a mixture of from more than 94.0 mole percent of a dimethylamino$(C_2-C_6)$methacrylamide and from 0.5 to less than 6 mole percent of a $(C_3-C_{12})$alkylenebis(methacrylamide).

21. The sequestrant of claim 20, wherein the sequestrant is the polymerized product of a mixture of about 95.6 mole percent dimethylaminopropylmethacrylamide and about 4.4 mole percent N,N'-hexamethylenebis(methacrylamide).

22. A pharmaceutical composition, comprising a therapeutically effective amount of the sequestrant of claim 1 and a pharmaceutically acceptable carrier.

23. The composition of claim 22, further comprising a therapeutically effective amount of a material that inhibits cholesterol biosynthesis.

24. The composition of claim 23, wherein the cholesterol synthesis inhibiting material is an HMG-CoA reductase inhibitor.

25. A pharmaceutical composition, comprising a therapeutically effective amount of the sequestrant of claim 9 and a pharmaceutically acceptable carrier.

26. The composition of claim 25, further comprising a therapeutically effective amount of a material that inhibits cholesterol biosynthesis.

27. The composition of claim 26, wherein the cholesterol synthesis inhibiting material is an HMG-CoA reductase inhibitor.

28. A method for lowering plasma cholesterol in a mammal, comprising orally administering to the mammal a therapeutically effective amount of a bile acid sequestrant comprising elongated matrix elements and an effective amount of crosslinking matrix elements crosslinked with the elongated matrix elements to render said sequestrant insoluble in water, and branch elements attached to the elongated matrix elements, said elongated matrix elements and attached branch elements being formed by polymeric chains of repeating units, said chains including units having the structural formula:

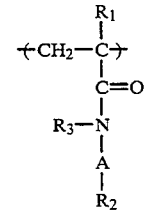

wherein
$R_1$ is H or $(C_1-C_8)$ alkyl;
A is

or

or

$R_2$ is

-continued or $$-\overset{R_7}{\underset{R_9}{N^{\pm}}}-R_8;$$

each occurrence of $R_3$, $R_4$, $R_5$, $R_6$, $R_7$ $R_8$ and $R_9$ is independently selected from the group consisting of H and $(C_1-C_8)$alkyl;

a is an integer from 1 to 20;
b is an integer from 1 to 10;
d is an integer from 1 to 10;
e is an integer from 1 to 5;
and wherein the crosslink matrix elements comprise crosslink matrix elements having the structural formula:

$$D + E - \underset{R_{10}}{\overset{|}{C}} - CH_2 \overset{}{\rightarrow}_2$$

or $$F + CH - CH_2 \overset{}{\rightarrow}_f;$$

wherein
D is $$+CHR_{11} \overset{}{\rightarrow}_g$$

or $$+ (CHR_{11} \overset{}{\rightarrow}_h O \overset{}{\rightarrow}_k + CHR_{12} \overset{}{\rightarrow}_i;$$

E is $$-O-$$

-continued or $$-\underset{R_{14}}{\overset{O}{\underset{|}{N-C}}}-;$$

F is phenylene, $(C_1-C_4)$alkylphenylene or benzenetriyl;
each occurrence of $R_{10}$, $R_{11}$, $R_{12}$ and $R_{14}$ is independently selected from the group consisting of H and $(C_1-C_8)$alkyl; and
f is 2 if f is phenylene or $(C_1-C_8)$alkylphenylene, and f is 3 if F is benzenetriyl;
g is an integer from 1 to 20;
h is an integer from 1 to 10;
i is an integer from 1 to 10;
j is an integer from 1 to 5;
and pharmaceutically acceptable salts thereof;
said sequestrant including less than 1.0 percent by weight water extractable polymer.

29. The method of claim 28, wherein the amount administered is between about 2 milligrams and about 125 milligrams per day per kilogram of body weight of the mammal.

30. The method of claim 28, further comprising administering to the mammal a therapeutically effective amount of a material that inhibits cholesterol biosynthesis by the mammal.

31. The method of claim 30, wherein the cholesterol synthesis inhibiting material is an HMG-CoA reductase inhibitor.

32. A method for lowering plasma cholesterol in a mammal, comprising orally administering to the mammal a therapeutically effective amount of the bile acid sequestrant of claim 9.

33. The method of claim 32, wherein the amount administered is between about 2 milligrams and about 125 milligrams per day per kilogram of body weight of the mammal.

34. The method of claim 32, further comprising administering to the mammal a therapeutically effective amount of a material that inhibits cholesterol biosynthesis by the mammal.

35. The method of claim 34, wherein the cholesterol synthesis inhibiting material is an HMG-CoA reductase inhibitor.

* * * * *